US010383845B2

(12) United States Patent
Ramu

(10) Patent No.: US 10,383,845 B2
(45) Date of Patent: Aug. 20, 2019

(54) AMELIORATING PERIODONTITIS BY LOCAL TREATMENT WITH WARFARIN AND/OR OTHER VITAMIN K OXIDE REDUCTASE INHIBITORS

(71) Applicant: Avner Ramu, Houston, TX (US)

(72) Inventor: Avner Ramu, Houston, TX (US)

( * ) Notice: Subject to any disclaimer, the term of this patent is extended or adjusted under 35 U.S.C. 154(b) by 79 days.

(21) Appl. No.: 15/970,933

(22) Filed: May 4, 2018

(65) Prior Publication Data

US 2018/0318253 A1 Nov. 8, 2018

Related U.S. Application Data

(60) Provisional application No. 62/502,289, filed on May 5, 2017.

(51) Int. Cl.
| | | |
|---|---|---|
| *A61K 31/37* | (2006.01) | |
| *A61Q 11/00* | (2006.01) | |
| *A61K 8/49* | (2006.01) | |
| *A61K 9/20* | (2006.01) | |
| *A61K 9/68* | (2006.01) | |

(52) U.S. Cl.
CPC .............. *A61K 31/37* (2013.01); *A61K 8/498* (2013.01); *A61K 9/0058* (2013.01); *A61K 9/20* (2013.01); *A61Q 11/00* (2013.01)

(58) Field of Classification Search
None
See application file for complete search history.

(56) References Cited

U.S. PATENT DOCUMENTS

| | | | | |
|---|---|---|---|---|
| 3,742,549 A | * | 7/1973 | Scopp ................... | A46B 9/028 15/167.1 |
| 2002/0022057 A1 | * | 2/2002 | Battey .................. | A61K 9/0056 424/490 |
| 2007/0258913 A1 | * | 11/2007 | Rossel ................. | A61K 31/122 424/49 |

OTHER PUBLICATIONS

Chávez de Paz et al., The Root Canal Biofilnn, p. 347-348, 2015 (Year: 2015).*
Ghimenti et al., Measurement of Warfarin in the Oral Fluid of Patients Undergoing Anticoagulant Oral Therapy, PLoS One, Dec. 2011 | vol. 6 | Issue 12 | e28182 (Year: 2011).*
Cao Z et al., Biochem J, 473:851-858, 2016.
Casper M, Czogalla KJ, Liphardt K, Muller J, Westhofen P, Watzaka M, Oldenburg, J. Thromb Res, 135:977-983, 2015.
Dogan GE, Demir T, Aksoy H, Saglam E, Laloglu E. Arch Oral Biol 70:125-129, 2016.
Dutton RJ et al., PNAS, 105:11933-11938, 2008.
Dutton RJ et al., PNAS, 107:297-301, 2010.
Eke PI et al., J Dent Res, 91:914-920, 2012.
Gibbons RJ and MacDonald JB. J Bacteriol 80:164-170, 1960.
Goodstadt L and Ponting CP., Trends in Biochem Sci, 29:289-292, 2004.
Goth A., Science, 101:383, 1945.
Hardman JG and Limbird LE., Goodman & Gilman's the pharmacological basis of therapeutics. Tenth Ed. McGrow-Hill. N.Y. 2001. pp. 1528; 2021.
Hatahet F et al,. Biochim Biophys Acta, 1844:1402-1414, 2014.
Higgins-Gruber SL et al., J Biol Chem, 285:31502-31508, 2010.
Hojo, K, Appl Microbiol, 103:1969-1974,2007.
Lagerlof F and Dawes C. J Dent Res 63:618-621, 1984.
Lentner C. Geigy Scientific Tables vol. 1. Eighth Ed. Ciba-Geigy. 1981. p. 114.
Lev M. J gen Microbiol, 20:697-703. 1959.
Li J et al., Org Biomol Chem, 12:5528-5535, 2014.
Li W et al., Nature, 463:507-512, 2010.
Lomonaco T et al., Plos one, 9:1-23, 2014.
Reardon-Robinson ME et al., J Biol Chem, 290:21393-21405, 2015.
Luong TT et al., J bacterial, 199:10, May 15, 2017.
Shiroza T et al., Biosci Biotechnol Biochem, 72:1826-1835, 2008.
Shoji M et al., BMC Microbiolgy, 10:152-163, 2010.
Tie J-k, Jin D-Y, and Stafford DW., J Biol Chem, 287:33945-33955, 2012.
Thijssen HH and Drittij-Reijnders MJ., Br J Nutr, 72:415-425, 1994.
Tribble GD et al., Future Microbiol, 8:607-620 2013.
Wu C et al., J Bacteriol, 193:3197-3206, 2011.
Wyss C. J. Clin Microbiol 30:2225-2229, 1992.
Sui, Yun-Peng, et al, "Antibacterial and Antitumor Activities of Biscoumarin and Dihydropyran Derivatives", Molecules 2015, 20, 17614-17626.
Cowan, Marjorie Murphy, "Plant Products as Antimicrobial Agents", Clinical Microbiology Reviews, vol. 12, No. 4. Oct. 1999, p. 564-582.

* cited by examiner

*Primary Examiner* — Jennifer A Berrios
(74) *Attorney, Agent, or Firm* — Richard A. Baker, Jr.

(57) ABSTRACT

A new indication for the Warfarin family of drugs is described. In patients suffering from chronic periodontitis, continued systemic medication with Warfarin causes a significant reduction in their chronic periodontitis, including reduction in the frequency and severity of gingival inflammation occurrences, and significant decrease in the buildup of dental plaque and tartar. Delivery of Warfarin or its analogs directly to the oral fluid using toothpaste, mouthwash, chewing gum, dental floss, toothbrush, pill, and other forms are described to reduce chronic periodontitis, dental plaque, and dental tartar.

7 Claims, 2 Drawing Sheets

AMELIORATING PERIODONTITIS BY LOCAL TREATMENT WITH WARFARIN AND/OR OTHER VITAMIN K OXIDE REDUCTASE INHIBITORS

RELATED APPLICATIONS

This patent application claims priority to U.S. Provisional Patent Application 62/502,289, entitled "Ameliorating Periodontitis by Local Treatment with Warfarin and/or Other Vitamin K Oxide Reductase Inhibitors", filed on May 5, 2017. This provisional patent application is incorporated herein by reference.

BACKGROUND

Technical Field

The formulations and devices described herein are directed for the pharmacological treatment of periodontitis and for reducing gingival inflammation and the buildup of dental plaque and tartar.

Description of the Related Art

Vitamin K and the growth of chronic Periodontitis causing bacteria. *Porphyromonas gingivalis* is one of the few major pathogens responsible for the development of chronic periodontitis. This Gram-negative anaerobe colonizes the dental plaque biofilms in the human oral cavity (see Tribble G D et al., *Future Microbiol*, 8:607-620 2013).

*Porphyromonas gingivalis* has a surface hemin-binding protein (HBP35) which contains a catalytic center for thioredoxin (see Shiroza T et al., *Biosci Biotechnol Biochem*, 72:1826-1835, 2008; and Shoji M et al., *BMC Microbiology*, 10:152-163, 2010). Recently Cao et al (Cao Z et al., *Biochem J*, 473:851-858, 2016) showed that thioredoxin-like transmembrane protein is involved in the recycling of oxidized vitamin K.

The growth of several types of bacteria was shown to be essentially dependent on the availability of vitamin K, and this growth was inhibited by compounds that block the recycling of oxidized vitamin K (M. Lev (Lev M *J gen Microbiol*, 20:697-703. 1959; Gibbons and MacDonald (Gibbons R J and MacDonald J B *J Bacteriol* 80:164-170, 1960).

Like these bacteria, the growth of *Porphyromonas gingivalis* is essentially dependent on the availability of vitamin K (C. Wyss (Wyss C. J. *Clin Microbial* 30:2225-2229, 1992; Hojo et al (Hojo, K, *Appl Microbiol*, 103:1969-1974, 2007), and is therefore expected to be inhibited by Warfarin that was found to be an efficient blocker of the recycling of oxidized vitamin K. In fact, patients treated with systemic Warfarin for thrombo-embolic diseases, had marked improvement of their periodontal disease.

However, none of these works considered approaches to ameliorating periodontitis by using Warfarin or its analogs to reduce vitamin K in oral fluid.

SUMMARY OF THE INVENTION

Warfarin, its analogs, or other VIKOR inhibitors are introduced to the oral fluid in sufficient concentration to reduce the availability of non-oxidized vitamin K for periodontitis causing bacteria. Warfarin is introduced using mouthwash, toothpaste, tooth brushes, chewing gum, dental floss, mini-capsules, pills, slow release devices.

A method for treating a patient suffering from gingivitis with a vitamin K oxide-reductase inhibitor and its delivery to oral fluid is described. The method is made of the steps of determining the presence of *Porphyromonas gingivalis* in the patient's oral cavity (by examining for plaque or tartar or by culturing the oral fluid) and delivering a vitamin K oxide-reductase inhibitor to the patient's oral fluid. The vitamin K oxide-reductase inhibitor could be Warfarin (in some embodiments the concentration of Warfarin in at least $1 \times 10\text{-}7M$), a Warfarin analog or similar. The vitamin K oxide-reductase inhibitor is introduced to the patient's oral fluid through toothpaste, mouthwash, a toothbrush, chewing gum, dental floss, a pill or similar mechanism.

A gingivitis treatment comprising a vitamin K oxide-reductase inhibitor and a mechanism to deliver vitamin K oxide-reductase inhibitor to *Porphyromonas gingivalis* in the oral fluid the patient's oral cavity. The vitamin K oxide-reductase inhibitor could be Warfarin (in some embodiments the concentration of Warfarin in at least $1 \times 10\text{-}7M$), a Warfarin analog or similar. The mechanism could be toothpaste, mouthwash, a toothbrush, chewing gum, dental floss, a pill or similar mechanism.

DETAILED DESCRIPTION OF THE INVENTION

Figure 1:
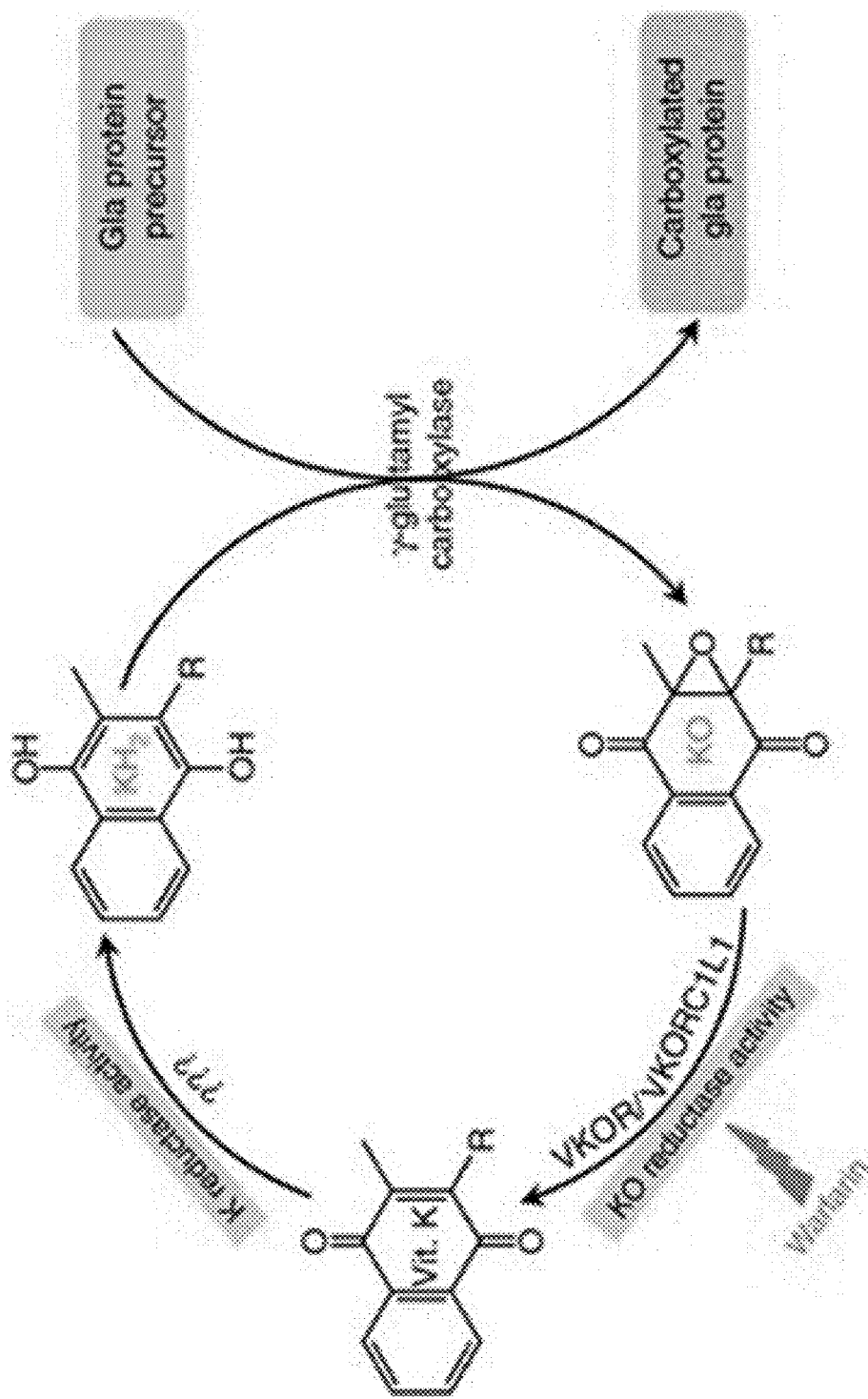
FIG. 1 is a diagram of the effect of warfarin on the recycling of oxidized vitamin K and on the carboxylation of the γ-carbon of the glutamic acid residues of certain proteins.

Original Observations and Postulations.

Periodontitis is one of the most common bacterial infections of humans and 47% of the US adult population is affected by some form of this disease (Eke P I et al., *J Dent Res*, 91:914-920, 2012).

I found that in patients suffering from chronic periodontitis, that a continued systemic medication with Warfarin (also known by the trade name Coumadin), causes a significant reduction in their chronic periodontitis, including reduction in the frequency and severity of gingival inflammation occurrences, and significant decrease in the buildup of dental plaque and tartar. Such observations had not been reported in the medical literature or anywhere else.

Most, if not all, of the biological effects of Warfarin were shown to be due to its ability to inhibit the Vitamin K Oxide Reductase (VKOR) enzymes. The described above therapeutic effects of the drug could be mediated by several different VKOR dependent mechanisms. Warfarin could indirectly block the Vitamin K dependent carboxylation of the precursor of Gla-Osteocalcin or of the precursor of Matrix-Gla Protein that may reach the mouth fluid from the blood or in the secretions of the salivary glands. Another possibility is that the concentration of Warfarin in the mouth fluid in Warfarin-treated patients is sufficient for inhibiting the growth of some periodontitis-causing bacteria.

There are a number of VKOR blockers listed in the Merck Index (13th edition) and elsewhere. These compounds can be arranged in three groups, 4-Hydroxycoumarin analogs, 1,3-Indandione analogs, and 2-hydroxy-1,4-Naphtoquinone analogs. The 4-Hydroxycoumarin analogs include at least Acenocoumarol, Brodifacoum, Bromadiolone, Coumatetalyl, Coumetarol, Cyclocumarol, Dicumarol, Difenacoum, Ethyl Biscoumacetate, Ethylidene Dicoumarol, Flocoumafen, Phenprocoumon, Tecarfarin, Tioclomarol, and Warfarin. The 1,3-Indandione analogs include at least Anisindione, Clorindione, Chlorophacinone, Diphenadione, Fluindione, Phenindione, and Pindone. The 2-hydroxy-1,4-Naphtoquinone analogs include at least 3-(3-cyclohexyl-propyl-2-hydroxy-1,4-Naphtoquinone, 3-(2-methyloctyl)-2-hydroxy-1,4-Naphtoquinone, and 3-[3-(decahydro-2-naphthyl)-propyl]-2-hydroxy-1,4-Naphtoquinone. All of these compounds could be used in place of Warfarin in this document.

Proposition.

Amelioration of Periodontitis, and of the frequency and severity of gingival inflammation occurrences, and of the buildup of dental plaque and tartar, could be achieved by the treatment of the patients with systemic administration of Warfarin or with other VKOR enzyme inhibitors. Based on the findings of Lomonaco (Lomonaco T et al., *Plos one*, 9:1-23, 2014) it appears that a concentration of less than $1\times10^{-7}$M of Warfarin in oral fluid is sufficient to be effective. But to assure effectiveness, a concentration of $3\times10^{-5}$M in the oral fluid is recommended. As the volume of the oral fluid is about 3 ml, that means a total dose of 10 μg of Warfarin to be delivered to the mouth fluid (which is less than 1/600 of the standard swallowed dose of Warfarin when used systematically to treat clotting).

In addition to alimentary route of the drug administration, other ways of drug delivery could be employed for achieving these therapeutic purposes. Therapeutic concentrations of Warfarin (or other VKOR enzyme inhibitors) in the oral fluid could also be achieved by the delivery of these drugs directly to the oral fluid by one of (but not only) the following methods: mouthwash, toothpaste, tooth brushes, chewing gum, dental floss, mini-capsules, pills, slow release devices. The advantage of delivery directly to the oral fluid is that this will not affect the rest of the body such as interfering with the blood clotting system.

Mouth Wash.

Mouthwash, mouth rinse, oral rinse or mouth bath, is a liquid which is held in the mouth passively or swilled around the mouth by contraction of the perioral muscles and/or movement of the head. A mouthwash product such as the commercially available Scope, Oral Essentials, Listerine or similar is modified to include Warfarin in a concentration sufficient to leave a concentration of $3\times10^{-5}$M in the oral fluid. A chlorhexidine compound could be used in conjunction with the Warfarin to assure adherence of the Warfarin to the dental surfaces.

Chewing Gum.

Chewing gum is a soft, cohesive substance designed to be chewed without being swallowed. Modern chewing gum is composed of gum base, sweeteners, softeners/plasticizers, flavors, colors, and, typically, a hard or powdered polyol coating. Its texture is reminiscent of rubber because of the physical-chemical properties of its polymer, plasticizer, and resin components, which contribute to its elastic-plastic, sticky, chewy characteristics. Warfarin is added to the chewing gum formula in a sufficient concentration to leave a concentration of $3\times10^{-5}$M in the oral fluid. Chewing gum that contains 10 microgram of Warfarin will provide adequate concentration of Warfarin in the mouth fluid for an extended period of time. 10 microgram of Warfarin is 1/600 of the dose necessary to slow the blood coagulation and therefore is risk-free, even if repeated several times a day. Because the chewing gum is kept in the mouth for an extended period of time, it affords the opportunity to dispense of the Warfarin to the dental surfaces for an extended period of time. Alternatively it could be administered from a slow release mini capsule that can be inserted into a periodontal pocket.

Dental Floss.

Dental floss, dental taps, or tooth floss, is a cord of thin filaments used to remove food and dental plaque from between teeth in areas a toothbrush is unable to reach. As the build-up of plaque between the teeth is the primary cause of dental disease, such as gingivitis and dental caries, the use of floss is commonly recommended in order to prevent these conditions from developing. Floss is often coated in wax (or similar substance), and the wax could be infused with Warfarin such that the act of flossing leaves Warfarin in the mouth. The concentration of the Warfarin in the wax needs to be sufficient to leave a concentration of $3\times10^{-5}$M in the oral fluid after flossing. It may also be possible to attach Warfarin directly to the filaments of the Dental floss.

Toothpaste.

Toothpaste is a paste or gel dentifrice used with a toothbrush as an accessory to clean and maintain the aesthetics and health of teeth. Toothpaste is used to promote oral hygiene: it serves as an abrasive that aids in removing the dental plaque and food from the teeth, assists in suppressing halitosis, and delivers active ingredients (most commonly fluoride) to help prevent tooth decay (dental caries) and gum disease (gingivitis). Warfarin could be added as an active ingredient of the toothpaste in sufficient concentrations to leave a concentration of $3\times10^{-5}$M in the oral fluid after brushing.

Toothbrush Head.

The toothbrush is an oral hygiene instrument used to clean the teeth, gums, and tongue. It consists of a head of tightly clustered bristles mounted on a handle which facilitates the cleaning of hard to reach areas of the mouth. In the last decade or two, toothbrushes have been introduced that dispense toothpaste when used. Toothbrush heads could also be coated with a coating to dispense a material. The material (or the toothpaste) dispensed could include Warfarin in sufficient concentrations to leave a concentration of $3\times10^{-5}$M in the oral fluid after brushing.

Mini-Pellet.

Furthermore, the Warfarin could be provided to the user through a slow release of the drug from a mini-pellet device inserted into a periodontal pocket. Warfarin is included in the mini-pellet formula in a sufficient concentration to maintain a concentration of $3\times10^{-5}$M in the oral fluid.

As the volume of the oral fluid is many fold smaller than the volume of the blood, it is obvious that for achieving the oral treatment goals suggested above, a direct delivery of the drug to the oral fluid, could achieve therapeutic concentrations of Warfarin (or of other VKOR enzyme inhibitors) in the oral fluid, with much lower total drug doses than those used in the systemic administration of the drug. It is unlikely that a significant portion of the drug delivered directly to the oral fluid will be absorbed into the blood. However even if all the drug delivered to the oral fluid will be absorbed to the blood, its quantity would be several fold smaller than that necessary to cause a significant reduction in the ability of the blood to coagulate.

Vitamin K and VKOR Inhibitors.

As indicated above, certain vital proteins (e.g. several of the blood-clotting factors) become functional only after carboxylation of the γ-carbon of several of their glutamic acid residues. This essential modification is carried out by an enzyme named γ-Glutamyl Carboxylase (GGCX). The activity of this enzyme is dependent on the presence of reduced Vitamin K, which is oxidized in this process to Vitamin K epoxide (Higgins-Gruber S L et al., *J Biol Chem*, 285:31502-31508, 2010).

Only the reduced form of Vitamin K promotes the activity of GGCX. Various mammalian tissues and several non-mammalian organisms contain an enzyme that can reduce the Vitamin K epoxide. This enzyme is named Vitamin K Oxide Reductase (VCOR). This enzyme is highly sensitive to inhibition by several 4-Hydroxycoumarin drugs, such as dicoumarol and Warfarin (Tie J-k, Jin D-Y, and Stafford D W., *J. Biol Chem*, 287:33945-33955, 2012).

Already in 1945 Goth reported that Dicumarol had marked antibacterial properties (Goth A., *Science*, 101:383, 1945). Although not known at that time, this report suggests that several types of bacteria may have a VKOR-like enzyme activity.

In 2004 Goodstadt and Ponting reported that VKOR family is widespread in life forms including prokaryotes, plants, vertebrates, some insects (such as *drosophila*), but not in fungi. In some bacteria, the VKOR domain is fused with the domain of thioredoxin oxidoreducases (Goodstadt L and Ponting C P., *Trends in Biochem Sci*, 29:289-292, 2004). Dutton et al showed that the bacterial homolog of VKOR, found in the bacterial cell envelope, is involved in the formation of structural disulfide bonds in a great number of proteins (Dutton R J et al., *PNAS*, 105:11933-11938, 2008). Further studies revealed the details of the structure and function of the bacterial VKOR (Li W et al., *Nature*, 463:507-512, 2010; Hatahet F et al., *Biochim Biophys Acta*, 1844:1402-1414, 2014).

In 2010 Dutton and el reported that the bacterial VKOR of several strains of mycobacteria was inhibited by Warfarin at concentration of 1.6-4.5 mM (Dutton R J et al., PNAS, 107:297-301, 2010). More recently Sui et al conducted a structure-activity study of the antibacterial activity of several Dicoumarol analogs (Sui Y-P et al., Molecules, 20:17614-17626, 2015).

Vitamin K and the Buildup of Dental Tartar.

Thijssen and Drittij-Reijnders studied the tissue distribution of vitamin K1 and Mnaquinone-4 (MK-4) in rats fed with vitamin K1. The highest MK-4 concentrations were found in the pancreas and in the salivary glands (Thijssen H H and Drittij-Reijnders M J., Br J Nutr, 72:415-425, 1994).

Casper et al (Casper M, Czogalla K J, Liphardt K, Muller J, Westhofen P, Watzaka M, Oldenburg, J. Thromb Res, 135:977-983, 2015) reported that VKORC1 was highly expressed in the salivary glands, but the γ-glutamyl carboxylase activity there was relatively low. It is therefore not clear whether the salivary glands are particularly active in producing secretory or non-secretory Gla (4-carboxyl glutamic acid)-containing proteins.

Yet according to the Human Protein Atlas, the Matrix-Gla protein (MGP) is highly expressed in the salivary glands. It was speculated that such salivary protein may be associated with the formation of subgingival dental calculus.

Dogan et al (Dogan G E, Demir T, Aksoy H, Saglam E, Laloglu E. Arch Oral Biol 70:125-129, 2016) found that concentration of MGP in the gingival cervical fluid of patients with no subgingival dental calculus was 80.74+/−16.20 pg/ml, while in patients with sublingual dental calculus it was 89.83+/−32.50 pg/ml. It is not clear whether this MPG was originated in the salivary glands or came from the blood.

These results suggest that the buildup of Dental tartar may depend only or also on other factor(s), which are currently unknown. Although possible, it is not known whether the reduction in Dental tartar in Warfarin-treated patients results from the inhibition of the formation of Gla-proteins that may be directly involved in the formation of Dental tartar, or whether, the inhibition of Dental tartar is a secondary result of the effect of the drug on other VKOR-dependent targets.

Vitamin K and the Buildup of Dental Plaque.

*Actinomyces oris*, is part of the oral microflora, and it participates in the formation of dental plaque. This organism creates a biofilm on the dental surface which provides a suitable matrix for colonization by other bacteria (Wu C et al., *J Bacteriol*, 193:3197-3206, 2011). The formation of the dental biofilm depends on certain bacterial proteins named Fimbriae. The Fimbriae are secreted by several types of bacteria such as *Actinomyces oris*.

To become active, the Fimbriae proteins need to undergo a specific type of folding that is mediated by a membrane-bound thiol-disulfide oxidoreductase (MdbA). Reoxidation of MdbA involves a bacterial Vitamin K epoxide reductase (VKOR)-like activity (Reardon-Robinson M E et al., *J Biol Chem*, 290:21393-21405, 2015; Luong T T et al., *J bacterial*, 199: to appear in print on May 15 2017).

As Warfarin and other 4-Hydroxycoumarin drugs were shown to inhibit bacterial VKOR and of the Growth of Vitamin K-dependent bacteria, it is most likely that the drugs inhibits the VKOR activity of *Actinomyces oris*, and/or the VKOR of other Fimbriae-forming bacteria and thus inhibit the formation of active Fimbriae, causing lake or reduced formation of Dental Plaque.

Warfarin Pharmacokinetics and Its Appearance in the Oral Fluid of Patients Treated with Continuous Medication with this Drug.

There is a good absorption of Warfarin from the gut (93+/−8%).

In the blood it is highly bound to proteins (99+/−1%).

The blood concentration of Warfarin has a half-life of 37+/−15 hours.

The fraction of the drug that is excreted in the urine is <2%.

Following a daily oral dose of 6.1+/−2.3 mg, Warfarin mean steady-state plasma concentration is 1.4+/−0.4 μg/ml (Hardman J G and Limbird L E., *Goodman & Gilman's the pharmacological basis of therapeutics*. Tenth Ed. McGrow-Hill. N.Y. 2001. pp 1528; 2021).

Figure 2:
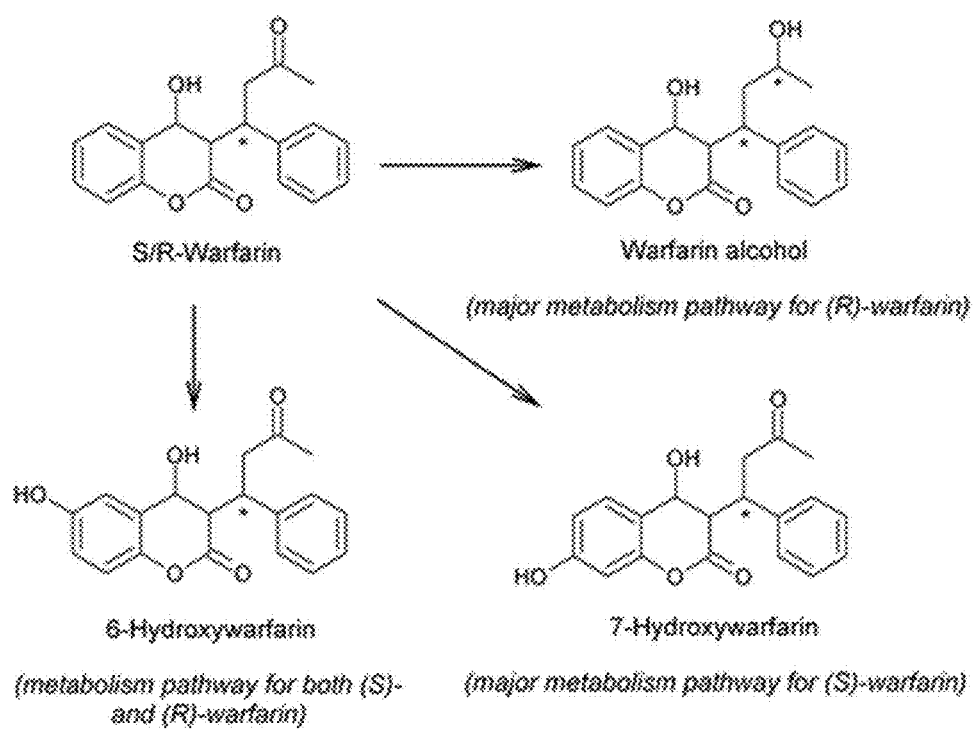
FIG. 2 is a drawing showing the pathways of metabolic inactivation of Warfarin.

It major elimination pathways are by metabolic conversions to inactive metabolites. See FIG. 2.

The anticoagulant activity of Warfarin correlates better with the concentration of the unbound drug in the blood, than with the total blood's Warfarin concentration.

Lomonaco et al from the University of Pisa (Lomonaco T et al., *Plos one*, 9:1-23, 2014), developed a method of determining Warfarin and some of its major metabolites in oral fluid. They collected blood and saliva samples from 14 patients undergoing Warfarin therapy. Among other things they also measured the concentration of unbound Warfarin in their patients' plasma and in their saliva.

They found:

1 Total plasma concentrations of Warfarin 1300+/−500 ng/ml (mean+/−S.D.)

2 Unbound plasma concentration of Warfarin 9+/−4 ng/ml.

3. Concentration of Warfarin in the saliva 3+/−2 ng/ml.

4. A linear correlation between the saliva's Warfarin concentration and the unbound plasma Warfarin concentration.

5. After stimulation of saliva production (by chewing gum for 6 min) the ratio of saliva's Warfarin concentration to the unbound plasma Warfarin concentration was 0.92. When saliva production was not stimulated this ratio was 0.48.

SUMMARY AND CONCLUSIONS

The medication of patients with Warfarin resulted in reduced frequency and severity of gingival inflammation, and of buildup of dental plaque and tartar.

There is evidence that reduced vitamin K promotes the growth of *Actinomyces oris* and of *Porphyromonas gingivalis*. It is therefore more than likely, that as shown for other types of prokaryotes, VKOR type enzyme activity is vital to their viability. It was reported that coumarin drugs such as Warfarin inhibits the VKOR activity of several types of bacteria.

An unbound Warfarin plasma concentration of: 9+/−4 ng/ml (~$3\times10^{-8}$M) is sufficient for effective inhibition of the human VKOR. As the concentrations of Warfarin in the oral fluid are of the same order of magnitude as the unbound Warfarin concentration in the plasma, it is likely that in patients undergoing Warfarin therapy, the growth of *Actinomyces oris* and/or *Porphyromonas gingivalis* is suppressed by the drug.

In addition to systemic medication, such concentration of Warfarin in the oral fluid could be achieved also by routes of drug administration other than swallowing tablets of the drug. Warfarin (or any other VKOR inhibitor) could be delivered directly to the oral fluid by one of several methods, such as mouthwash, tooth paste, dental floss, tooth brushes, or other methods for getting the Warfarin into the oral fluid.

Safety of the suggested approach

|  | Plasma | Oral fluid | Ratio Plasma/Oral fluid |
| --- | --- | --- | --- |
| Volume | ~3000 ml | <3 ml | >1000 |
| Protein | ~66 g/L | ~2.5 g/L | >28 |
| Albumin | ~44 g/L | ~7 mg/L | >6000 |

Oral Fluid values from Lagerlof F and Dawes C. *J Dent Res* 63:618-621, 1984; and Lentner C. *Geigy Scientific Tables* Vol 1. Eighth Ed. Ciba-Geigy. 1981. P 114.

As the volume of the oral fluid is many fold smaller than the volume of the blood, it is obvious that by direct delivery of the drug to the oral fluid, it is possible to achieve oral fluid Warfarin concentrations that would effectively inhibit the growth of *Actinomyces oris* and of *Porphyromonas gingivalis* without systemic accumulation of a significant amount of the drug. Therefore, no significant inhibit the human VKOR, or reduction in the ability of the blood to coagulate is expected with such a treatment.

The foregoing devices and operations, including their implementation, will be familiar to, and understood by, those having ordinary skill in the art.

The above description of the embodiments, alternative embodiments, and specific examples, are given by way of illustration and should not be viewed as limiting. Further, many changes and modifications within the scope of the present embodiments may be made without departing from the spirit thereof, and the present invention includes such changes and modifications.

The invention claimed is:

1. A method of treating a patient suffering from gingivitis with a vitamin K oxide-reductase (VKOR) inhibitor, the method comprising the steps of: determining the presence of *Porphyromonas gingivalis* in the patient's oral cavity; and
    delivering 10 micrograms of a VKOR inhibitor to the patients oral fluid using a toothbrush.

2. The method of claim 1 wherein the VKOR inhibitor is Warfarin.

3. The method of claim 1 wherein the VKOR inhibitor is a Warfarin analog.

4. A gingivitis treatment composition comprising:
    10 micrograms of a vitamin K oxide-reductase (VKOR) inhibitor; and
    a toothbrush to deliver the 10 micrograms of the VKOR inhibitor to the oral fluid in a patients oral cavity.

5. The gingivitis treatment composition of claim 4, wherein a head of the toothbrush is coated with the VKOR inhibitor.

6. The gingivitis treatment composition of claim 4 wherein the VKOR inhibitor is Warfarin.

7. The gingivitis treatment composition of claim 4 wherein the VKOR inhibitor is a Warfarin analog.

* * * * *